US005733566A

United States Patent [19]

Lewis

[11] Patent Number: 5,733,566
[45] Date of Patent: *Mar. 31, 1998

[54] CONTROLLED RELEASE OF ANTIPARASITIC AGENTS IN ANIMALS

[75] Inventor: Danny H. Lewis, Hartselle, Ala.

[73] Assignee: Alkermes Controlled Therapeutics Inc. II, Cambridge, Mass.

[*] Notice: The term of this patent shall not extend beyond the expiration date of Pat. No. 5,686,092.

[21] Appl. No.: 550,504

[22] Filed: Oct. 30, 1995

Related U.S. Application Data

[63] Continuation-in-part of Ser. No. 374,439, Jan. 19, 1995, abandoned, which is a continuation-in-part of Ser. No. 981,082, Nov. 24, 1992, abandoned, which is a division of Ser. No. 523,249, May 15, 1990, Pat. No. 5,288,496.

[51] Int. Cl.$^6$ ........................................................ A61F 2/00
[52] U.S. Cl. .................. 424/426; 424/422; 424/424; 424/425; 424/486; 424/489; 424/499
[58] Field of Search ............................... 424/426, 422, 424/424, 425, 486, 489, 499

[56] References Cited

U.S. PATENT DOCUMENTS

| | | | |
|---|---|---|---|
| 4,150,108 | 4/1979 | Graham | 424/22 |
| 4,329,332 | 5/1982 | Couvreur et al. | 424/9 |
| 4,389,330 | 6/1983 | Tice et al. | 427/213.36 |
| 4,489,055 | 12/1984 | Couvreur et al. | 424/7.1 |
| 4,530,840 | 7/1985 | Tice et al. | 514/179 |
| 4,542,025 | 9/1985 | Tice et al. | 424/78 |
| 4,675,189 | 6/1987 | Kent et al. | 424/490 |
| 4,677,191 | 6/1987 | Tanaka et al. | 528/361 |
| 4,683,288 | 7/1987 | Tanaka et al. | 528/361 |
| 4,857,335 | 8/1989 | Bohm | 424/455 |
| 5,178,872 | 1/1993 | Ohtsubo et al. | 424/408 |
| 5,252,701 | 10/1993 | Jarrett et al. | 528/354 |
| 5,275,820 | 1/1994 | Chang | 424/426 |
| 5,288,496 | 2/1994 | Lewis | 424/426 |

FOREIGN PATENT DOCUMENTS 0 525 307  2/1993  European Pat. Off. .

OTHER PUBLICATIONS

Arnold, R.G., "Controlled–Release New Animal Drugs," *J. Controlled Release* 8:85–90 (1988).

Baggott, J.D., "Veterinary Drug Formulations for Animal Health Care: An Overview," *J. Controlled Release* 8:5–13 (1988).

Benz et al., "Use of Ivermectin in Cattle, Sheep, Goats, and Swine," In: *Ivermectin and Abamactin*, W.C. Campbell (ed.), Springer Verlag, NY, pp. 216–229 (1989).

Carter et al., "Controlled Release Parenteral Systems for Veterinary Applications," *J. Controlled Release* 8: 15–22 (1988).

George et al., "Biology and Control of Ticks of Regulatory Importance," *Current Research Information Systems (CRIS) Project Outlines and Annual Reports*, Dept of Agriculture, Accession No. 0145604; 6205–32000–006–00D, 43. pgs. (Oct. 1, 1989 to Sep. 30, 1994).

Gopalratnam et al., "Microencapsulation of Astiban Acid for the Treatment of *Schistosomiasis mansoni*," *Appl. Biochem. Biotech.* 10:213–220 (1984).

Guillot et al., "Biology and Control of Biting Flies Affecting Livestock," *Current Research Information Systems (CRIS) Project Outlines and Annual Reports*, Dept. of Agriculture, Accession No. 0143821; 6205–32000–009–00D, 35 pgs. (Oct. 1, 1990 to Sep. 30, 1995).

Laakso et al., "Biodegradable Microspheres VI: Lysosomal Release of Covalently Bound Antiparasitic Drugs from Starch Microparticles," *J. Pharm. Sci.* 76(2): 134–140 (1987).

Lewis, D.H., "Controlled Release Microspheres for Veterinary Applications," *Vet. Pharmacol. in the Pharm. Industry*, 9th Biennial Symp., Kalamazoo, MI, pp. 93–109 (Jun. 16–18, 1994).

Lewis, D.H., "Controlled Release of Bioactive Agents from Lactide/Glycolide Polymers," In: *Biodegradable Polymers as Drug Delivery Systems*, Chasin et al. (eds.), Marcel Dekker, Inc., NY, pp. 1–41 (1990).

Miller et al., "A Sustained Release Ivermectin Implant for Livestock Pet Control," In: *Controlled Release Delivery Systems*, Roseman and Mansdoy (eds.), Marcel Dekker, NY, pp. 223–236 (1983).

Nixon, J.R. and Hassan, M., "The effect of preparative technique on the particle size of thiabendazole microcapsules," *J. Pharm. Pharmacol.* 32:856–857 (1980).

Shoop, W.L. and Mrozik, H., "Veterinary Pharmacology in Animal Health Discovery: Structure and Activity of Avermectins and Milbemycins in Animal Health," *Vet. Pharmacol. in the Pharm. Industry, 9th Biennial Symp.*, Kalamazoo, MI, pp. 35–51 Jun. 16–18, 1994).

*Primary Examiner*—D. Gabrielle Phelan
*Attorney, Agent, or Firm*—Sterne, Kessler, Goldstein & Fox P.L.L.C.

[57] ABSTRACT

A delivery system for providing antiparasitic agents to animals is provided and a method of treating parasitic infections in animals using such delivery systems is described. The delivery system is particularly useful for treatment with avermectins and milbemycins in lactide/glycolide polymeric matrices.

29 Claims, No Drawings

CONTROLLED RELEASE OF ANTIPARASITIC AGENTS IN ANIMALS

CROSS-REFERENCE TO RELATED APPLICATIONS

This Application is a continuation-in-part application of U.S. application Ser. No. 08/374,439, filed Jan. 19, 1995, now abandoned which is a continuation-in-part application of U.S. application Ser. No. 07/981,082, filed Nov. 24, 1992, now abandoned which is a divisional application of U.S. application Ser. No. 07/523,249, filed May 15, 1990, now U.S. Pat. No. 5,288,496.

BACKGROUND OF THE INVENTION

Field of the Invention

This invention is directed to a controlled-release delivery system which is used to provide antiparasitic, and especially anthelmintic agents to animals.

Parasitic Diseases

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often serious infection in various species of animals.

The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridis, Oxyuris, Ancylostoma, Uncinaria, Toxascaris and Parascaris. Certain of these, such as Nematodirus, Cooperia and Oesophagostomum, attack primarily the intestinal tract. Others, such as Haemonchus and Ostertagia, are more prevalent in the stomach. Others, such as Dictyocaulus, are found in the lungs. Still other parasites may be located in other tissues and organs of the body such as the heart and blood vessels, subcutaneous and lymphatic tissue, and the like.

The parasitic infections known as helminthiases lead to anemia, malnutrition, weakness, weight loss, severe damage to the walls of the intestinal tract and other tissues and organs, and, if left untreated, may result in death of the infected host.

The most common genera of parasites of the gastrointestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filarial worms such as Wuchereria, Brugia, Onchocerca and Loa, Dracunculus and extra-intestinal stages of the intestinal worms Strongyloides and Trichinella.

Onchocerciasis is a major blinding disease that, until recently, has been essentially untreatable. Approximately 85 million people live in areas endemic for onchocerciasis and 18 million people are infected with *Onchocerca volvulus*. Onchocerciasis causes blindness or visual loss in one to two million of these infected people. More than half of the inhabitants of hyper-endemic areas will become blind before death, and life expectancy of those who are blind is one-third that of their sighted peers (Taylor, H. R., et. al., *Science* 250:116–118).

Current Delivery Systems for Antiparasitic Agents

A common route of administration for the treatment of parasitic infection and infestation is the oral route. Antiparasitic compounds thus have been administered orally in a unit-dosage form such as a capsule, bolus, or tablet, or as a liquid drench. The drench is normally a solution suspension or dispersion of the active ingredient, usually in water, together with a suspending agent. Active parasitic agents have also been administered via animal feedstuffs, where the compound is intimately dispersed in the feed or used as a top-dressing, or in the form of pellets which may then be added to the finished feed or, optionally, fed separately.

Antiparasitic compounds have also been administered parenterally, for example, by intraluminal, intramuscular, intratracheal, or subcutaneous injection, in which the active ingredient is dissolved or dispersed in a liquid carrier vehicle. Antiparasitic agents have also been administered topically in the form of ointments, powders, and liquids absorbed through the skin (i.e., transdermally).

A drawback of the above methods of administration is the need for repeated dosing with its attendant difficulties of handling with animals, children, and other such subjects for which administration may be difficult, inefficient drag utilization, residual drug accumulation, and non-biodegradability, such that the dosage system, as with implant devices, must be mechanically removed as in some current methods. Further, variable release characteristics for multiple agents administered in a single dose is difficult to achieve by standard delivery formulations.

Therefore, a need exists for a delivery device that overcomes the problems described above. Such a device provides an effective amount of an antiparasitic agent(s) in a single dosing form, requires minimal handling, and provides efficient drug utilization. Such a device is preferably biodegradable.

Controlled-Release Technology

In the field of human and veterinary medicine many advantages are offered by controlled release technology. First, controlled release of a pharmaceutical agent allows less frequent dosing and thus minimizes handling of animals and repeated treatment of humans. Further, controlled release treatment results in more efficient drug utilization. Further, less of the compound remains as a residue. Still further, controlled release technology offers the opportunity to administer and release two or more different drugs, each having a unique release profile, or to release the same drug at different rates or for different durations, by means of a single dosage unit.

Despite these advantages, however, few controlled release formulations for parenteral administration have been developed for commercial use in the veterinary industry or in human medicine. An exception is in the beef industry in the field of growth promotion. In this industry, nondegradable sustained release implants of growth promoters have been used commercially.

Biodegradable sustained release microparticles for delivery of growth promoters and contraceptives are in the process of development in the cattle industry (U.S. Pat. No. 5,288,496; Lewis, D. H., in *Biodegradable Polymers as Drug Delivery Systems*, eds. Chasen, M. and Langer, R.

(1990), pp. 1–141 Marcel Dekker, Inc., New York). Leupron™ (TAP, Inc.) is a biodegradable microsphere product for delivery of LHRH polypeptide to humans for control of prostate cancer in males.

Many controlled release products in the process of development for human application are based on biodegradable polymer excipients. Prostate cancer and endometriosis, for example, have been successfully treated in humans (see above). Other human products in the developmental stage, including vaccines, growth hormones, contraceptives, and CNS agents, are based on biodegradable injectable microspheres (Lewis, D. H., in *Biodegradable Polymers as Drug Delivery Systems*, eds. Chasen, M. and Langer, R. (1990), pp. 1–141 Marcel Dekker, Inc., New York).

The present invention provides the advantages of controlled release technology for the treatment of parasitic diseases.

Avermectin and Milbemycins

The term "avermectin" (previously referred to in the patent literature as C-076) is used to describe a series of compounds isolated from the fermentation broth of an avermectin-producing strain of *Streptomyces avermitilis* and derivatives thereof. The morphological characteristics of the culture are completely described in U.S. Pat. No. 4,310,519, incorporated herein by reference.

The avermectins are a series of macrolides, each of which is substituted at the 13 position with a 4'-(α-L-oleandrosyl)-α-L-oleandrose group. Avermectins and derivatives have a high degree of anthelmintic and antiparasitic activity. Novel derivatives have been described in U.S. Pat. Nos. 4,199,569, 4,206,205, 4,427,663, 4,587,247, and 5,288,710, all of which are incorporated herein by reference.

Milbemycin or B-41, is a substance which is isolated from the fermentation broth of a milbemycin-producing strain of Streptomyces. The microorganism, the fermentation conditions, and the isolation procedures are fully described in U.S. Pat. Nos. 3,950,360 and 3,984,564, which are incorporated herein by reference. Carbohydrate derivatives of milbemycin and of 13-hydroxy milbemycin have been described in U.S. Pat. No. 4,134,973, which is incorporated herein by reference.

The avermectins and milbemycins are related 16-membered macrocyclic aglycones. The milbemycins and avermectins appear to possess the same mode of action. They both have acaricidal, insecticidal, and nematocidal activities. Thus, they can be used in the treatment of endoparasitic and ectoparasitic infections in veterinary and human medicine. These compounds have been designated "endectosides". The substituted avermectins have high activity against the parasites discussed above, and in addition are also active against Dirofilaria in dogs; Namatospiroides, Syphacia, Aspiculuris in rodents; the arthropod ectoparasites of animals and birds such as ticks, mites, lice, fleas, and blowfly; in sheep Lucilia sp.; biting insects and such migrating diperous larvae as Hypoderma sp. in cattle; Gastrophilus in horses; and Caterebra sp. in rodents. The avermectins am also useful against parasites which infect humans. The compounds are also effective against arthropods parasitizing man, biting insects and, other dipterous pests causing annoyance to man.

For a discussion of the structure and activity of avermectins and milbemycins in animal health, see, Shoop, W. L., et al., in 9th Biennial Symposium of the American Academy of Veterinary Pharmacology and Therapeutics, Jun. 16–18, 1994, pp. 35–51.

Ivermectin is a semisynthetic avermectin that was first introduced commercially for veterinary use in 1975. The mechanism of action of this compound rendered it effective against parasites resistant to other antiparasitic agents. This agent has been released in over 60 countries for use in cattle, sheep, goats, horses, pigs, dogs, camels, reindeer, bison and humans. Ivermectin is a safe and effective drug for the mass treatment of Onchocerciasis and when used on an individual basis, it reduces the ability of the treated person to transmit Onchocerca Volvulus infection (Taylor et al., above). The antiparasitic activity of ivermectin administered subcutaneously, orally, and topically as a therapeutic agent against nematode and arthropod parasites of cattle has been thoroughly documented (Williams, J. C., et. al., *Am. J. Vet. Res.* 53:793–795 (1992)). Use of ivermectin for prophylaxis of nematode infections in cattle via an experimental sustained release bolus indicated that ivermectin was highly effective in preventing the establishment of nine nematode parasite species in multiply-exposed cattle (Williams et al., above).

Avermectin-$B_1$ is a natural product and is the starting material for ivermectin. It is a more potent nematicide than ivermectin. It is used in both animal and crop protection. Moxidectin is a semisynthetic whose starting material, nemadectin, is a fermentation product from *Streptomyces cyaneogriseus*. Doramectin, 25-cyclohexyl-avermectin-$B_1$, is a fermentation product from a mutant of *Streptomyces avermitilis*. It is the fourth endecticide (avermectin or milbemycin) to be introduced for production for animals. For a more complete discussion, see Shoop, W. L., et al. (above), incorporated herein by reference.

The animal health applications of ivermectin have been reviewed (Benz, G. W., et at., in *Ivermectin and Abamectin*, Campbell, W. C., ed., Springer-Verlag, New York (1989), pp. 215–295, incorporated herein by reference). Ivermectin has been used in oral formulations such as in oral solution as for the treatment and control of gastrointestinal nematodes, lungworms, grubs, and sucking lice. The agent has also been topically applied in a liquid form for the treatment and control of gastrointestinal nematodes, lungworms, grubs, sucking and biting lice, chorioptic and sarcoptic mange mites and as an aid in control of ticks. A sustained release bolus form has also been used (Williams, J. C. et al., *Am. J. Vet. Res.* 53:793–795 (1992)) to deliver ivermectin at a steady-state rate. The boluses are designed to be delivered orally into the distal pharynx or anterior esophagus. In sheep, a liquid form has been used for the treatment and control of gastrointestinal nematodes, lungworms, nasal bots and itch mites. An injectable formulation has also been used in sheep. This was administered subcutaneously and was indicated for the treatment and control of gastrointestinal nematodes, lungworms, nasal bots, mange mites and itch mites. A liquid formulation for goats has been used as in sheep. Injectable formulations have also been used in pigs as a treatment against gastrointestinal roundworms, lungworms, kidney worms, lice and mites.

However, none of these treatment modalities meets the need for a delivery system for antiparasitic agents as described above.

SUMMARY OF THE INVENTION

In view of the above-described state of the art, the objects of the invention are to provide an antiparasitic composition that combines the advantages of minimal repetitive administration, efficient drug utilization, minimal handling, and minimal drug residue. Accordingly, a biodegradable, injectable, parenterally administrable, delivery system has been developed for the sustained release of antiparasitic agents in animals, which includes the advantages of controlled release of one or more active agents and an unexpectedly low tissue residue of the antiparasitic agent in various organs and at the injection site at the end of the treatment.

The invention comprises an injectable, long-acting, microparticle composition for the delivery of antiparasitic agents. The invention provides the antiparasitic agent incorporated within a biodegradable polymeric matrix formed into microparticles (also known as microcapsules or microspheres).

Preferred biodegradable matrix materials for the microparticles include homopolymers or copolymers of lactic/glycolic acid, polycaprolactone, polydioxonene, polyorthoesters, polyanhydrides, and natural polymers including albumin and casein. Especially preferred are homopolymers or copolymers of lactic/glycolic acid.

Microparticles of the present invention can be designed to provide unique release characteristics. The parameters which are varied to produce the characteristics include the polymer composition, polymer molecular weight, polymer-:drug ratio, and microparticle diameter. Heterogeneous compositions of uniquely designed microparticles are also encompassed in the present invention. Any permutation of the parameters designed to produce a desired release profile is within the scope of the invention. For example, all microparticles in the final formulation may be of approximately similar size but have different drug loadings (wt %). Alternatively, the same weight percent may be found in all of the microparticles but the sizes may differ. Further, heterogeneous populations of microparticles may include sub-populations formed with different polymer matrices, etc.

The invention, accordingly, provides a method for adjusting the duration of release from less than a week to several months by manipulation of various parameters. The amount (level) of agent released can also be controlled by manipulation of various parameters. The parameters include polymer composition, polymer molecular weight, polymer:drug ratio, and microparticle diameter.

The invention thus provides a method for controlling the steady-state levels of antiparasitic agents in animals and for providing antiparasitic agents in a multiphasic manner.

Accordingly, unique microspheres are provided wherein one or more of the above parameters have been varied. Thus, mixed populations can be combined into single dosage forms or different types of microspheres are co-administered. The same antiparasitic agent can be incorporated into the different microparticle types that are combined in the final formulation or co-administered. Thus, multiphasic delivery of the same antiparasitic agent can be achieved.

The invention, however, also further provides a method for delivering two or more active agents at predetermined release rates with the release of each drug being at a different rate and duration by design. Compositions and methods are provided wherein more than one antiparasitic agent is delivered or an antiparasitic agent(s) is administered with other bioactive agents such as growth promoters and antibiotics. The additional bioactive agent(s) can be unencapsulated, encapsulated separately, or co-encapsulated with the antiparasitic agent. If separately encapsulated, the matrix may be the same or different for each agent. As above, any of the parameters may be varied to produce unique microparticles having specific release characteristics for the given encapsulated agent. Thus, distinct multiphasic release patterns can be obtained for each of the agents encapsulated in mixed microparticle populations for single or co-administration. The invention thus provides a wide range of possible in vivo release profiles.

Accordingly, the invention provides a method of treating parasitic infection in an animal by treating such animals with injectable, biodegradable microparticles, wherein such microparticles are loaded with at least one antiparasitic agent. Populations of microparticles with different active antiparasitic agents or other types of bioactive agents can be blended to form a composite formulation. Parameters can be varied so that mixed populations of microparticles are formed and so that not all encapsulated agents are released at the same rate, if desired, or such that the same agent is released at different rates in a single dosage form or by co-administration.

Other agents include antibiotics, growth promoters, and vaccines.

The microparticle composition includes all types of antiparasitic agents. Broad classes of agents include ectoparasiticides and endoparasiticides. In preferred embodiments of the invention, the antiparasitic agent is an anthelmintic, and especially a nematocide. The invention, however encompasses any agent active against endo- and ectoparasitic anthropods, annelids, insects, acarids, and protozoans.

In preferred embodiments of the invention, the active agent is an avermectin or a milbemycin.

The invention is useful in all animals including, but not limited to cattle, swine, horses, deer, sheep, goats, dogs, cats, reindeer, camels, bisons, poultry and humans.

DETAILED DESCRIPTION OF THE PREFERRED EMBODIMENTS

In order to provide a clearer and consistent understanding of the specification and claims, including the scope to be given such terms, the following definitions are provided.

The term "administer" is intended to mean any method for introducing the compositions of the present invention into a subject by parenteral (intravenous, intramuscular, intraperitoneal, or subcutaneous) introduction. When administration is for the purpose of treatment, administration may be either for prophylactic or therapeutic purpose. When provided prophylactically the substance is provided in advance of any symptom. The prophylactic administration of the substance serves to prevent or attenuate any subsequent symptom. When provided therapeutically the substance is provided at (or shortly after) the onset of a symptom. The therapeutic administration of the substance serves to attenuate any actual symptom.

The term "animal" is intended to mean any living creature that is susceptible to parasitic infection or infestation and thus susceptible to treatment by the administration of the agents of this invention. Foremost among such animals are food animals. However, the invention is not intended to be so limiting, it being within the scope of the present invention to apply the compositions of the invention to any and all animals which may experience the benefit of the compositions or methods of the invention. These include work animals, wild animals, zoo animals, pets, and humans. Wild animals are included, as these may be vectors for parasite transmission to domesticated animals.

The term "food animal" is intended to mean any animal that is consumed as a source of protein in the diet of humans or other animals. Typical food animals include bovine animals, for example cattle; ovine animals, for example sheep; porcine, for example pigs; fowl, for example chickens and turkeys; rabbit, and the like.

The term "microparticles" is intended to mean solid particles which contain an active agent, either in solution or in crystalline form. The active agent is dispersed or dissolved within the polymer which serves as the matrix of the particle. The active material is released from the microparticles by diffusion, leaching or erosion of the matrix or by a combination of these mechanisms.

The term "microparticle" is synonymous with the terms "microsphere" and "microcapsule". This type of device has been described in the following references, which are incorporated herein by reference: Luzzi, L. A., *J. Pharm. Psy.* 59:1367 (1970); U.S. Pat. No. 4,530,840; Lewis, D. H., "Controlled Release of Bioactive Agents from Lactides/Glycolide Polymers" in *Biodegradable Polymers as Drug Delivery Systems*, Chasin, M. and Langer, R., eds., Marcel Decker (1990); U.S. Pat. No. 4,675,189; Beck et al., "Poly (lactic acid) and Poly(lactic acid-co-glycolic acid) Contraceptive Delivery Systems," in *Long Acting Steroid Contraception*, Mishell, D. R., ed., Raven Press (1983); U.S. Pat. No. 4,758,435; U.S. Pat. No. 3,773,919; U.S. Pat. No. 4,474,572.

The microparticle product of the present invention usually has a spherical shape, although irregularly-shaped microparticles are possible. The microparticles vary in size, ranging from submicron to 1000 micron diameters. Preferably, submicron to 250 mm diameter microparticles, are desirable, allowing administration by injection with a standard gauge needle.

The microparticles can thus be prepared by any method which produces microparticles in a size range acceptable for use in an injectable composition. Injection may be accomplished with standard gauge needles used for administering liquid compositions parenterally.

The term "antiparasitic agent" is intended to mean any agent that treats parasitic infection or infestation. Parasites include endoparasites and ectoparasites. Species include, but are not limited to, helminths, protozoans, annelids, and arthropods. Subspecies include nematodes and acarids. Thus, antiparasitic agents include those effective against these parasites. Preferred agents include the anthelmintics, and especially nematocides.

The polymeric matrix material of the microparticles present invention must be a biocompatible and biodegradable polymeric material. The term "biocompatible material" is defined as a polymeric material which is not toxic to an animal and not carcinogenic. The matrix material should be biodegradable in the sense that the polymeric material should degrade by bodily processes to products readily disposable by the body and should not accumulate in the body. The biodegraded products also should be biocompatible with the body in the sense that the polymeric matrix is compatible with the body.

The term "controlled-release" is intended to mean the property of the microparticles described herein that is the result of the design of the microparticles so that the design enables a deliberate and pro-determined release profile. The parameters of the release profile are total amount of release, rate of release, and total duration of release. As described herein, controlled release is achieved by specific variations in one or more of the physical parameters encompassed in the microparticles of the present invention. These include polymer composition, polymer:drug ratio, and microsphere size.

The term "biodegradable" is intended to mean the property by which a component is capable of being metabolized in vivo to excreted or otherwise harmless by-products such that the original material is not retained in the body. The term is used in its ordinary sense.

The present invention provides compositions for treating parasitic infections in animals comprising biodegradable parenterally administrable microparticles loaded with an antiparasitic agent and methods using the compositions.

The present invention provides advantages over compositions and methods known in the art such as, biodegradability, injectability, minimum loss of dose during treatment, efficient drug utilization, the ability to mix unique microparticles containing the same or different drugs, the ability to program release and to vary release (multiphasic release patterns) of the same or different drugs, and minimal drug residue in tissues.

The present invention encompasses the use of any biodegradable polymer. Suitable examples of polymeric matrix materials include poly(glycolic acid), poly-d,l-lactic acid, poly-l-lactic acid, copolymers of the foregoing, poly (aliphatic carboxylic acids), copolyoxalates, polycaprolactone, polydioxonene, poly(ortho carbonates), poly(acetals), poly(lactic acid-caprolactone), polyorthoesters, poly(glycolic acid-caprolactone), polydioxonene, polyanhydrides, polyphosphazines, and natural polymers including albumin, casein, and some waxes, such as, glycerol mono- and distearate, and the like. Various commercially available poly (lactide-co-glycolide) materials (PLGA) may be used in the method of the present invention. For example, poly (d,l-lactic-co-glycolic acid) is commercially available from Medisorb Technologies International L.P. (Cincinnati, Ohio). A suitable product commercially available from Medisorb is a 50:50 poly (d,l) lactic co-glycolic acid known as MEDISORB® 5050 DL. This product has a mole percent composition of 50% lactide and 50% glycolide. Other suitable commercially available products are MEDISORB® 65:35 DL, 75:25 DL, 85:15 DL and poly(d,l-lactic acid) (d,l-PLA). Poly(lactide-co-glycolides) are also commercially available from Boehringer Ingelheim (Germany) under its Resomer mark, e.g., PLGA 50:50 (Resomer RG 502), PLGA 75:25 (Resomer RG 752) and d,l-PLA (Resomer RG 206), and from Birmingham Polymers (Birmingham, Ala.). These copolymers are available in a wide range of molecular weights and ratios of lactic acid to glycolic acid.

A preferred polymer for use in the practice of this invention is poly(d,l-lactide-co-glycolide). It is preferred that the molar ratio of lactide to glycolide in such a copolymer be in the range of from about 95:5 to about 50:50.

The molecular weight of the polymeric matrix material is of some importance. The molecular weight should be high enough so that it forms satisfactory polymer coatings, i.e., the polymer should be a good film former. Usually, a satisfactory molecular weight is in the range of 5,000 to 500,000 daltons. However, since the properties of the film are also partially dependent on the particular polymeric material being used, it is very difficult to specify an appropriate molecular weight range for all polymers. The molecular weight of a polymer is also important from the point of view that molecular weight influences the biodegradation rate of the polymer. For a diffusional mechanism of drug release, the polymer should remain intact until all of the drug is released from the microparticles and then degrade. The drug can also be released from the microparticles as the polymeric excipient bioerodes. By an appropriate selection of polymeric materials a microparticle formulation can be made such that the resulting microparticles exhibit both diffusional release and biodegradation release properties. This is useful in affording multiphasic release patterns.

A variety of methods are known by which compounds can be encapsulated in microparticles. In these methods, the material to be encapsulated (drugs or other active agents) is generally dispersed or emulsified, using stirrers, agitators, or other dynamic mixing techniques, in a solvent containing a wall-forming material. Solvent is then removed from the microparticles, and thereafter the microparticle product is obtained.

An example of a conventional microencapsulation process for pharmaceutical preparations is shown in U.S. Pat. No. 3,737,337, incorporated herein by reference. The substances to be encapsulated or embedded are dissolved or dispersed in the organic solution of the polymer (phase A), using conventional mixers, including (in the preparation of dispersion) vibrators and high-speed stirrers, etc. The dispersion of phase (A), containing the core material in solution or in suspension, is carried out in the aqueous phase (B), again using conventional mixers, such as high-speed mixers, vibration mixers, or even spray nozzles, in which case the particle size of the microgranulates will be determined not only by the concentration of phase (A), but also by the emulsate or microparticulate size. With conventional techniques for the microencapsulation of biological or pharmaceutical agents (active agents), the microparticles form when the solvent containing an active agent and a polymer is emulsified or dispersed in an immiscible solution by stirring, agitating, vibrating, or some other dynamic mixing technique, often for a relatively long period of time.

Conventional methods for the construction of microparticles of the invention are also described in U.S. Pat. No. 4,389,330, and U.S. Pat. No. 4,530,840, incorporated herein by reference. U.S. Pat. No. 4,389,330 describes the following method. The desired agent is dissolved or dispersed in an appropriate solvent. To the agent-containing medium is added the polymeric matrix material in an amount relative to the active ingredient which gives a product of the desired loading of active agent. Optionally, all of the ingredients of the microparticle product can be blended in the solvent medium together. Suitable solvents for the agent and the polymeric matrix material include organic solvents such as acetone, halogenated hydrocarbons such as chloroform, methylene chloride and the like, aromatic hydrocarbon compounds, halogenated aromatic hydrocarbon compounds, cyclic ethers, alcohols, ethyl acetate and the like. Preferred solvents for the agent are methylene chloride or ethyl acetate.

The mixture of ingredients in the solvent is emulsified in a continuous-phase processing medium; the continuous-phase medium being such that a dispersion of microdroplets containing the indicated ingredients is formed in the continuous-phase medium. Naturally, the continuous-phase processing medium and the organic solvent must be immiscible, and most commonly is water although nonaqueous media such as xylene and toluene and synthetic oils and natural oils can be used. Usually, a surfactant is added to the continuous-phase processing medium to prevent the microparticles from agglomerating and to control the size of the solvent microdroplets in the emulsion. A preferred surfactant-dispersing medium combination is a 1 to 10 wt. % poly (vinyl alcohol) in water mixture. The dispersion is formed by mechanical agitation of the mixed materials. An emulsion can also be formed by adding small drops of the active agent-wall forming material solution to the continuous phase processing medium. The temperature during the formation of the emulsion is not especially critical but can influence the size and quality of the microparticles and the solubility of the drug in the continuous phase. Of course, it is desirable to have as little of the agent in the continuous phase as possible. Moreover, depending on the solvent and continuous-phase processing medium employed, the temperature must not be too low or the solvent and processing medium will solidify or the processing medium will become too viscous for practical purposes, or too high that the processing medium will evaporate, or that the liquid processing medium will not be maintained. Moreover, the temperature of the medium cannot be so high that the stability of the particular agent being incorporated in the microparticles is adversely affected. Accordingly, the dispersion process can be conducted at any temperature which maintains stable operating conditions, which preferred temperature being about 30° C. to 60° C., depending upon the drug and excipient selected.

The dispersion which is formed is a stable emulsion and from this dispersion the organic solvent immiscible fluid can optionally be partially removed in the first step of the solvent removal process. The solvent can easily be removed by common techniques such as heating, the application of a reduced pressure or a combination of both. The temperature employed to evaporate solvent from the microdroplets is not critical, but should not be that high that it degrades the agent employed in the preparation of a given microparticle, nor should it be so high as to evaporate solvent at such a rapid rate to cause defects in the wall forming material. Generally, from 5 to 75%, preferably 1 to 25% of the solvent is removed in the first solvent removal step.

After the first stage, the dispersed microparticles in the solvent immiscible fluid medium are isolated from the fluid medium by any convenient means of separation. Thus, for example, the fluid can be decanted from the microparticle or the microparticle suspension can be filtered. Still other, various combinations of separation techniques can be used if desired.

Following the isolation of the microparticles from the continuous-phase processing medium, the remainder of the solvent in the microparticles is removed by extraction. In this step, the microparticles can be suspended in the same continuous-phase processing medium used in step one, with or without surfactant, or in another liquid. The extraction medium removes the solvent from the microparticles and yet does not dissolve the microparticles. During the extraction, the extraction medium with dissolved solvent can optionally be removed and replaced with fresh extraction medium. This is best done on a continual basis. Obviously, the rate of extraction medium replenishment or a given process is a variable which can easily be determined at the time the process is performed and, therefore, no precise limits for the rate must be predetermined. After the majority of the solvent has been removed from the microparticles, the microparticles are dried by exposure to air or by other conventional drying techniques such as vacuum drying, drying over a desiccant, or the like. This process is very efficient in encapsulating the agent since core loadings of up to 80 wt. %, preferably up to 60 wt. % are obtained.

Alternatively, and preferably, controlled release microparticles containing an active agent can be prepared through the use of static mixers as described in U.S. application Ser. No. 08/338,805, incorporated herein by reference. Static or motionless mixers consist of a conduit or tube in which is received a number of static mixing agents. Static mixers provide homogeneous mixing in a relatively short length of conduit, and in a relatively short period of time. With static mixers, the fluid moves through the mixer, rather than some part of the mixer, such as a blade, moving through the fluid.

A static mixer can be used to create an emulsion. When using a static mixer to form an emulsion, several factors determine emulsion particle size, including the density and viscosity of the various solutions or phases to be mixed, volume ratio of the phases, interfacial tension between the phases, static mixer parameters (conduit diameter; length of mixing element; number of mixing elements), and linear velocity through the static mixer. Temperature is a variable because it effects density, viscosity, and interfacial tension. The controlling variables are linear velocity, sheer rate, and pressure drop per unit length of static mixer.

In order to create microparticles containing an active agent, an organic phase and an aqueous phase are combined. The organic and aqueous phases are largely or substantially immiscible, with the aqueous phase constituting the continuous phase of the emulsion. The organic phase includes an active agent as well as a wall-forming polymer or polymeric matrix material. The organic phase can be prepared by dissolving an active agent in an organic or other suitable solvent, or by forming a dispersion or an emulsion containing the active agent. The organic phase and the aqueous phase are pumped so that the two phases flow simultaneously through a static mixer, thereby forming an emulsion which comprises microparticles containing the active agent encapsulated in the polymeric matrix material. The organic and aqueous phases are pumped through the static mixer into a large volume of quench liquid to extract or remove the organic solvent. Organic solvent may be removed from the microparticles while they are washing or being stirred in the quench liquid. After the microparticles are washed in a quench liquid, they are isolated, as through a sieve, and dried.

The process of the present invention whereby microparticles are prepared using a static mixer can be carried out for a variety of techniques used to encapsulate active agents. The process is not limited to the solvent extraction technique discussed above, but can be used with other encapsulation techniques. For example, the process can also be used with a phase separation encapsulation technique. To do so, an organic phase is prepared that comprises an active agent suspended or dispersed in a polymer solution. The non-solvent second phase is free from solvents for the polymer and active agent. A preferred non-solvent second phase is silicone oil. The organic phase and the non-solvent phase are pumped through a static mixer into a non-solvent quench liquid, such as heptane. The semi-solid particles are quenched for complete hardening and washing. Examples of using such a process are provided as Examples 11–14 in 08/338,805. The process of microencapsulation may also include spray drying, solvent evaporation, a combination of evaporation and extraction, and melt extrusion.

A highly preferred microencapsulation process is referred to in Example 5 and Table 1 herein. The process involves the use of a static mixer with a single solvent. This process is described in detail in U.S. application Ser. No. 08/338,805, herein incorporated by reference.

An alternative process involves the use of a static mixer with co-solvents. This process outlined below, is described in U.S. application Ser. No. 08/298,787, herein incorporated by reference. In this process for preparing biodegradable microparticles comprising a biodegradable polymeric binder and a biologically active agent, a blend of at least two substantially non-toxic solvents, free of halogenated hydrocarbons, is used to dissolve both the agent and the polymer. The solvent blend containing the dissolved agent and polymer is dispersed in an aqueous solution to form droplets. The resulting emulsion is then added to an aqueous extraction medium preferably containing at least one of the solvents of the blend, whereby the rate of extraction of each solvent is controlled, whereupon the biodegradable microparticles containing the biologically active agent are formed. The process has the advantages that less extraction medium is required because the solubility of one solvent in water is substantially independent of the other and solvent selection is increased, especially with solvents that are particularly difficult to extract.

More particularly, this method for preparing microparticles comprises preparing a first phase comprising a biodegradable polymeric encapsulating binder and an active agent dissolved or dispersed in a blend of at least two mutually miscible organic solvents free from halogenated hydrocarbons and having limited water solubility; preparing a second phase comprising an aqueous solution of (1) a hydrophilic colloid or (2) a surfactant; combining said first phase and said second phase under the influence of mixing means to form an emulsion in which said first phase is discontinuous and said second phase continuous; and isolating said discontinuous first phase in the form of microparticles.

A first solvent component of the solvent blend is a poor solvent for the active agent, but is a good solvent for the biodegradable polymer used herein. A second solvent component of the solvent blend is a good solvent for both the active agent and the polymer. These solvents must be: (1) mutually miscible with one another, (2) capable, when blended, of dissolving or dispersing the active agent, (3) capable, when blended, of dissolving polymeric matrix material, (4) chemically inert to the active agent, (5) biocompatible, and (6) substantially immiscible with the quench liquid, e.g., having a solubility of no more than about 0.1 to 25%. Solvents other than halogenated hydrocarbons are preferred.

As stated above, in order to create microparticles containing an active agent, an organic phase and an aqueous phase are combined. The organic and aqueous phases are largely or substantially immiscible, with the aqueous phase constituting the continuous phase of the emulsion. The organic phase includes the active agent as well as the wall forming polymer, i.e., the polymeric matrix material. The organic phase is prepared by dissolving or dispersing the active agent(s) in the organic solvent system of the present invention. The organic phase and the aqueous phase are combined under the influence of mixing means.

The invention provides durations of action ranging from less than a week to several months depending upon the type of microsphere selected. In a preferred embodiment, the microspheres are designed to afford antiparasitic effect in animals over a period of a few days to one year, and preferably 30 to 270 days. The duration of action can be easily controlled by manipulation of the polymer composition, polymer:drug ratio and microsphere size. The bloodstream level of agent can also be controlled by varying these parameters.

The invention provides a multiphasic delivery system which provides pulsed doses of desired antiparasitic agent (s), thus eliminating the need for consecutive treatments. This is accomplished by providing mixed populations of microspheres wherein the sub-populations are constructed by varying the parameters described above. Thus, the release rates and drug levels vary among the sub-populations of microspheres.

The same matrix type can be designed to contain various drug:polymer ratios. Thus, the blend includes sub-populations of microspheres with the same matrix material but with different drug loads (wt %). Alternatively, the drug load is constant but the microparticle size is varied so that sub-populations are blended to include microspheres of various sizes.

Alternatively, sub-populations of microspheres can be blended wherein sub-populations are formed with different matrices but with either or both of the other parameters held constant or varied. Within any given formulation, sub-populations are thus possible with one or more of the parameters held constant or varied to produce the desired release profile. Since duration of drug release and level are controlled by microparticle diameter, weight percent of the drug, and matrix type, any permutation of these parameters is within the scope of the invention and would be understood to be within the scope of the invention by the person of ordinary skill in the art.

Such mixed populations are used to deliver the same or different anti-parasitic agents in the same formulation. Thus, any given formulation can be designed to treat different parasitic infections by providing different agents. The release rates and levels of each agent is controlled by encapsulating the agent or agents in the appropriate microsphere designed as described above.

Further, other biologically active agents can be included in the formulations and encapsulated according to the desired release profile. These include agents that potentiate the anti-parasitic effect or that ameliorate or prevent side effects of the agents. Such agents also include unrelated agents such as antibiotics, growth promoters, and vaccines.

Examples of growth-promoters include estradiol benzoate, 17b-estradiol, trenbolone acetate, zeranol, testosterone and testosterone derivatives or combinations thereof. However, growth promoters also encompass non-steroid growth promoters such as, but not limited to, bovine growth hormone and porcine growth hormone.

Examples of antibiotics include oxytetracycline, tetracycline, ampicillin, gentamicin, penicillin, tylson, erythromycin and spectinomycin.

Examples of vaccines include those which are of cellular, viral or bacterial origin, specifically *Pasteurella multocide, Pasteurella haemolytica, Haemophilus influenzae, Haemophilus ducreyi, Escherichia coli, Salmonella abortus ovis,* and IBR-BVD-PI3 virus antigens.

Other active agents that are encompassed within the invention include, but are not limited to, vitamins such as Vitamin $B_{12}$, and anti-inflammatory agents such as hydrocortisone.

It is also understood that the various agents (if more than one agent is present in the formulation) can be co-encapsulated, separately encapsulated, or non-encapsulated. If separately encapsulated, the microsphere could be of a different design than the microsphere of the first agent (i.e., one or more of the above parameters are varied from the parameters used to form the microspheres containing the first agent).

Thus, in addition to release of all of the single agent or multiple agents at the same rate and to the same level, multiphasic and multilevel release patterns are obtainable for any and all agents included in a given blended formulation (i.e., for single agents and additional agents included in the given formulation).

It is also understood that such blended delivery can be accomplished by the administration of a heterogeneous blended population, by co-administration of two or more homogeneous populations or two or more blended formulations, or by sequential administration of these types of formulations.

The amount of antiparasitic agent incorporated in the microparticles usually ranges from less than 1 wt % to as high as 95 wt. %, preferably 10 to 60 wt. %. By weight % is meant parts of drug per parts of polymer by weight. For example, 10 wt. % would mean 10 parts drug per 90 parts polymer by weight. The preferred range is 25–60 wt % of drug.

Examples of formulations with different weight percentages of specific drugs include 18% and 52% loaded microspheres. Further examples include formulations with different polymer compositions, for example, 65:35 and 95:5 lactide:glycolide polymer. Different drug types are also included. Examples of blends of drug types include ivermectin and estradiol benzoate, an animal growth promoter.

The agent-bearing microparticles are produced as a dry material. Prior to administration to an animal or group of animals, the microparticles are suspended in an acceptable pharmaceutical liquid vehicle, either aqueous or oil based, and then the suspension is injected into the desired portion of the body of the animal. The liquid injection vehicle can be any pharmaceutically acceptable vehicle that does not allow significant solubilization of the polymeric matrix. The vehicle includes, but is not limited to, water, saline, carboxymethylcellulose and water, and oils, such as vegetable oil, mineral oil, and fish oil.

In a preferred embodiment, administration of the antiparasitic agent to animals by the methods of the invention is achieved by a single administration of the loaded microparticles. The microparticles then release the agent(s) in a constant or pulsed manner into the animal. This eliminates the need for repetitive injections.

The amount of agent administered depends on the parasite (s), animal species, agent, length of time of treatment, and weight, age, and health of the animal. Since the present invention is concerned with a unique method of treating parasitic infections in animals by administering antiparasitic agents in a biodegradable microparticle formulation involving encapsulating the agents, one skilled in the art is well aware of the dosages required to treat a particular animal with an agent. Commonly, the agents are administered in milligram to gram amounts.

Endoparasitic infections and ectoparasitic infestations are treated by the compositions and methods of the invention. Any endoparasitic infection or ectoparasitic infection is amenable to treatment. Foremost among such endoparasites are protozoans, helminths, including platyhelminths and nemahelminths, and annelids. Among the ectoparasites, arthropods and insects are included. Preferable species include ticks, mites, fleas, grubs, screw worms, and other boring or invasive insects. Thus, the parasiticides that are encompassed in the compositions and methods of the present invention include those effective against the above parasitic infestations and infections and protect or treat warm blooded animals against infection and infestation by helminths, nematodes, acarids, and endo- and ectoparasitic arthropods.

The nematodes most commonly found to be the infecting agents of ruminants include Haemonchus and Ostertagia generally found in the abomasum; Cooperia, Trichostrongylus and Nematodirus generally found in the intestinal tract, and Dictyocaulus found in the lungs. In non-ruminant animals, important nematodes include Toxocara and Ancylostoma in the intestine and Dirofilaria in the heart of dogs; Ascaris in the intestine of swine, Ascaridia and Heterakis in the intestine of poultry; and large and small strongyles in equines. Treatment of animals to prevent infestation thereof by the above nematodes or to reduce or control the proliferation of these infecting agents in animals is thus an important and desirable advantage of the present invention.

Besides controlling helminths and nematodes, the present invention also controls arthropod endoparasitic infestations such as cattle grub and ectoparasitic infestations such as psoroptic mange.

Suitable antiparasitic agents include but are not limited to active antiparasitic 16-membered macrocyclic lactones. Avermectins are preferred. Preferred avermectins include, but are not limited to, abamectin, ivermectin, MK-397, and MK-244. MK-397 and MK-244 are disclosed in U.S. Pat. No. 4,427,663, incorporated herein by reference. MK-244 is also disclosed as the benzoate salt in U.S. Pat. No. 5,288,710, incorporated herein by reference. Abamectin is disclosed in U.S. Pat. No. 4,310,519 as avermectin B1a/B1b, incorporated herein by reference and ivermectin is disclosed in U.S. Pat. No. 4,199,569, as 23,22-dihydroavermectin B1a/B1b, incorporated by reference. All antiparasitic compounds in these patents are encompassed by the present invention. Also encompassed are compounds disclosed in U.S. Pat. Nos. 4,587,247, 4,134,973, and 4,206,205, all incorporated herein by reference.

Highly preferred avermectins include ivermectin or 22, 23-dihydro-avermectin $B_1$, abamectin or avermectin $B_1$ and doramectin or 25-cyclohexyl-avermectin $B_1$. Also preferred antiparasitic are the milbemycins. Highly preferred milbemycins include moxidectin or 23-methoxime LL-F2849a milbemycin, milbemycin D or 22, 23-dihydro-13-dioxy-avermectin $B_{1B}$ aglycone, milbemycin $A_3/A_4$5-oxime, and milbemycin $A_3/A_4$. Further included are active ingredients selected from LL-F28249 α-λ compounds, 23-oxo and 23-imino derivatives of LL-F28249 α-λ compounds. Of course the invention also includes these compounds in any combination thereof.

The invention provides antiparasitic activity to all animals subject to parasitic infestation or infection. Such animals include, but are not limited to, cattle, swine, horses, sheep, goats, dogs, reindeer, camels, bisons, cats, mice, guinea pigs, hamsters, gerbils and the like. Animals include domestic farm animals, food animals, zoo animals, pets and wild animals.

In using the avermectins and milbemycins of this invention, the individual components in the fermentation broth may be isolated and purified. Alternatively, mixtures of the individual avermectins or milbemycins may be used. It is not necessary to completely separate the various avermectins or milbemycins obtained from the purification of the fermentation broth. Generally, there is obtained a mixture containing two or more of the avermectins or milbemycins, but having other unrelated compounds excluded therefrom, and such mixture may be used for the treatment of parasitic diseases as described herein.

The avermectins contemplated for the invention can have a broad spectrum of activity against many internal parasites at low dosage levels and in many different animals. At levels of about 2.5 mg. per kg. of animal body weight, concentrated mixtures of avermectins are fully active in sheep against *Haemonchus contortus, Ostertagia circumcincta, Trichostrongylus axei, Trichostrongylus colubriformis, Cooperia* spp., and *Oesophagostomum columbianum*. Similarly in cattle at dosages as low as 0.043 mg./kg. C-076 B2 is fully active against *Ostertagia ostertagi, Trichostrongylus axei, Trichostrongylus colubriformis, Oesophagostomum radiatum* and *Dictyocaulus viviparus*. In addition, a horse infected with bots (*Gastrophilus intestinalis* and *Gastrophilus haemorrhoidalis*), large and small strongyles and Oxyuris was successfully treated with 10 mg/kg (about 1% active compounds by weight) of a mixed concentrate of C-076 compounds, and a dog infected with the microfilarial stage of heart-worm (*Dirofilaria immitis*) was successfully treated with a single oral dose at 10 mg/kg (about 1% active compounds by weight) of a mixed concentrate of C-076 compounds. In rodents, such as mice, infections of Syphacia, Nematospiroides and Aspiculuris are successfully treated by the oral administration of the C-076 compounds or of the concentrates obtained from the extraction of the mycelia.

The microparticles of this invention have significant parasiticidal activity as anthelmintics, ectoparasiticides, insecticides and acaricides, in human and animal health.

The following examples further describe the materials and methods used in carrying out the invention. The examples are not intended to limit the invention in any manner.

EXAMPLES

Example 1

Preparation of 50% by Weight Theoretical Loaded Microparticle Formulation

Twenty-five grams, (25 g) of 95:5 d,l-PLGA and 25 g of ivermectin were codissolved in 196 g ethyl acetate in an Erlemeyer flask at 52° C. The drug/polymer solution was added to a 1000 ml glass jacketed reactor containing 550 g of 5% aqueous polyvinyl alcohol containing 9.7 g of ethyl acetate. Reactor contents were stirred with an overhead stir motor and the temperature was maintained at 52° C. by a circulating bath. After the emulsion had been stirred for about 2 minutes, the emulsion size (as determined by light microscopy) was found to be in the desired size range (less than 300 μ). The stir speed was reduced to avoid further size reduction of the sterilized emulsion. After stirring for a total of 4 minutes, the reactor contents were pressure-transferred into 40 liters of water at 12° C. After stirring for 20 minutes, the hardened microspheres were isolated and the product then transferred into 20 liters of water at 12° C. After approximately 3 hours, the second wash was transferred onto a sieve stack composed of 25, 45, 90, 150, and 212 micron (μ) openings. The product on the sieves was washed with copious amounts of cold water to separate the different sizes of microspheres. After drying on the sieves overnight, the different fractions were collected and drying was continued under vacuum at room temperature. Formulations with other drug levels were prepared by simply adjusting the polymer/drug ratio.

Example 2

65:35 d,l-PLGA Matrix

Microparticles were produced by the method of Example 1 except that a different biodegradable polymer matrix was utilized. A 65:35 d,l-PLGA polymer was used in place of the 95:5 polymer indicated in Example 1.

Example 3

100 d,l-PLA Matrix

Microparticles were produced by the method of Example 1 except that the 100% lactide homopolymer was used as the matrix material.

Example 4

Blends of Microspheres With Different Drug Percent by Weight

In addition to single component formulations, useful compositions can be achieved by blending individual formulations based on different drug contents (% by weight). SRO91-69, for example, a product tested in dogs was produced by blending an 18% drug-loaded batch with a 52% drug-loaded batch in a ratio of 25:75.

Example 5

Preparation of Microparticles with Static Mixer

A series of microparticle formulations was prepared by means of a static mixer apparatus rather than the rotating agitator described in Example 1. Table 1 describes the process conditions for several batches of anthelmintic-loaded microparticles.

TABLE 1

PREPARATION OF MICROSPHERES

| Batch No. | Polymer[1] | Drug[2] | Drug Loading, | Flow Rate ml/min | |
|---|---|---|---|---|---|
| SRO 91 | Type | Type | wt % | Org.[3] | Aq |
| 117 | 54:46 | A | 44.2 | 132 | 330 |
| 119 | 54:46 | A | 29.8 | 132 | 330 |
| 121 | 54:46 | B | 44.4 | 132 | 330 |
| 123 | 54:46 | B | 30.2 | 132 | 330 |
| 126 | 65:35 | A | 53.2 | 88 | 165 |
| 129 | 85:15 | B | 53.8 | 132 | 330 |
| 131 | 85:15 | B | 40.6 | 132 | 330 |
| 135 | 75:25 | B | 43.4 | 132 | 330 |
| 137 | 75:25 | B | 30.2 | 132 | 330 |
| 139 | 75:25 | A | 44.2 | 132 | 330 |
| 141 | 75:25 | A | 30.7 | 132 | 330 |

[1]Lactide: glycolide ratio
[2]A = ivermectin; B = 4-epi-acetylamino-4-deoxy-avermectin $B_1$
[3]Organic solvent = ethyl acetate

What is claimed is:

1. An injectable controlled-release composition comprising: microparticles, wherein said microparticles comprise a biodegradable polymeric matrix, wherein said composition comprises an antiparasitic agent within said matrix, and wherein release of said agent is essentially dependent upon diffusion from, leaching from or erosion of the matrix or by a combination of these mechanisms.

2. An injectable controlled-release composition comprising microparticles, wherein said microparticles comprise a biodegradable polymeric matrix, wherein said composition comprises two or more antiparasitic agents, and wherein each of said agents is separately microencapsulated in said polymeric matrix such that each of said microparticles contains a single antiparasitic agent.

3. The composition of claim 2, wherein the microparticles containing one agent are formed from a different polymeric material than the microparticles containing a second agent.

4. An injectable controlled-release composition comprising microparticles, wherein said microparticles comprise a biodegradable polymeric matrix, wherein said composition comprises two or more antiparasitic agents, wherein all of said antiparasitic agents is co-microencapsulated in said polymeric matrix such that each of said microparticles contains each of said antiparasitic agents, and wherein release of said agents is essentially dependent upon diffusion from, leaching from or erosion of the matrix, or a combination of these mechanisms.

5. The composition of any of claims 1–4, wherein said composition contains a biologically active agent in addition to said antiparasitic agent.

6. The composition of claim 5, wherein said additional agent is unencapsulated.

7. The composition of claim 5, wherein said additional agent is co-encapsulated with said antiparasitic agent.

8. The composition of claim 5, wherein said additional agent is separately microencapsulated from said antiparasitic agent.

9. The composition of claim 5, wherein said additional agent is selected from the group consisting of antigens, antibiotics, and growth promoters.

10. The composition of any of claims 1–4, wherein the polymeric matrix material of said microparticle is selected from the group consisting of poly-d,l-lactic acid, poly-L-lactic acid, polyglycolic acid, copolymers of mixed d,l-lactic acid and glycolic acid, copolymers of L-lactic acid and glycolic acid, copolyoxalates, polycaprolactone, poly (lactic acid-caprolactone), poly(glycolic acid-caprolactone), casein and albumin.

11. The composition of any of claims 1–4, wherein said microparticles are loaded with 1 to 75 wt. % of said agent based on the weight of said polymeric matrix.

12. The composition of any of claims 1–4, wherein said microparticles range in size from 1 to 250 microns.

13. The composition of any of claims 1–4, wherein said microparticles are formulated in a liquid injection vehicle.

14. The composition of any of claims 1–4, wherein said liquid vehicle is selected from the group consisting of physiological saline solution, and an aqueous solution of carboxymethyl cellulose with a surfactant.

15. The composition of any of claims 1–4, wherein said microparticles are suitable for administration by intramuscular injection.

16. The composition of any of claims 1–4, wherein said microparticles are suitable for administration by subcutaneous injection.

17. The composition of any of claims 1–4, wherein said antiparasitic agent is selected from the group consisting of avermectins and milbemycins.

18. The composition of claim 17, wherein said avermectin is selected from the group consisting of ivermectin, abamectin, and doramectin.

19. The composition of claim 17, wherein said milbemycin is selected from the group consisting of moxidectin, milbemycin D, milbemycin $A_3/A_4$, 5-oxime and milbemycin $A_3/A_4$.

20. The composition of any of claims 1–4, wherein said liquid vehicle is an oil selected from the group consisting of sesame oil, peanut oil, soybean oil, cottonseed oil, corn oil, sunflower oil, mineral oil, fish oil, triglyceride and substituted triglyceride.

21. A method of treating parasitic infection or infestation in an animal comprising administering the composition of any of claims 1–4 to said animal.

22. A method for introducing and maintaining effective blood levels of an antiparasitic compound in an animal comprising administering the composition of any of claims 1–4 to said animal.

23. The injectable controlled-release composition of claim 1, wherein said microparticles are solid microspheres.

24. The injectable controlled-release composition of claim 2, wherein said microparticles are solid microspheres.

25. The injectable controlled release composition of claim 4, wherein said microparticles are solid microspheres.

26. The composition of claim 1, wherein said antiparasitic agent is in the form of a dispersion within said matrix.

27. The composition of claim 1, wherein said antiparasitic agent is a nematocide.

28. The composition of claim 1, wherein said antiparasitic agent is an avermectin.

29. The composition of claim 28, wherein said avermectin is ivermectin.

* * * * *